United States Patent [19]

Cipullo

[11] Patent Number: 5,491,268
[45] Date of Patent: Feb. 13, 1996

[54] PROCESS FOR REMOVAL OF ACIDIC COMPOUNDS FROM PHENOL PROCESS STREAMS

[75] Inventor: Michael J. Cipullo, Prattville, Ala.

[73] Assignee: General Electric Company, Pittsfield, Mass.

[21] Appl. No.: 311,335

[22] Filed: Sep. 23, 1994

[51] Int. Cl.$^6$ .................................................. C07C 37/70
[52] U.S. Cl. ........................ 568/758; 568/749; 568/750; 568/754; 568/759
[58] Field of Search ..................... 568/749, 753, 568/754, 759, 795, 798, 799, 801, 758, 750

[56] References Cited

U.S. PATENT DOCUMENTS

| | | | |
|---|---|---|---|
| 2,937,142 | 5/1960 | Rios | 568/758 |
| 3,202,719 | 8/1965 | Jones | 568/758 |
| 3,442,958 | 5/1969 | Choo | 568/758 |
| 3,878,854 | 4/1975 | Albein et al. | 131/266 |
| 3,969,422 | 7/1976 | Neuzil | 568/750 |
| 4,124,770 | 11/1978 | Miyake et al. | 568/758 |
| 4,191,843 | 3/1980 | Kwantes et al. | 568/728 |
| 4,356,331 | 10/1982 | Inoue et al. | 568/758 |
| 4,375,568 | 3/1983 | Izod et al. | 568/758 |
| 4,766,254 | 8/1988 | Faler et al. | 568/724 |
| 4,847,433 | 7/1989 | Kissinger | 568/727 |
| 5,008,470 | 4/1991 | Powell et al. | 568/727 |
| 5,105,026 | 4/1992 | Powell et al. | 568/727 |
| 5,124,490 | 6/1992 | Cipullo | 568/758 |
| 5,336,813 | 8/1994 | Cipullo et al. | 568/703 |

FOREIGN PATENT DOCUMENTS 2058722  4/1981  United Kingdom ................... 568/758

*Primary Examiner*—Werren B. Lone

[57] ABSTRACT

A process for purifying phenol, phenol-type compounds, and substituted phenol and phenol-type compounds of contamination by components more acidic than the phenol component comprising treating a phenol containing process stream by contacting the stream with an amphoteric porous inorganic oxide.

16 Claims, No Drawings

PROCESS FOR REMOVAL OF ACIDIC COMPOUNDS FROM PHENOL PROCESS STREAMS

FIELD OF THE INVENTION

The present invention relates to a process for the removal of acidic impurities from phenol containing process streams. More particularly, the present invention relates to a process for the removal of acidic impurities from phenol containing process streams using a solid adsorbent whereby the acidic impurities are adsorbed thereon and the process stream is rendered essentially free of undesired acidic impurities.

BACKGROUND OF THE INVENTION

Phenol is commercially manufactured by any one of seven different processes. The seven processes used to manufacture phenol involve different aromatic starting materials and generally involve a step requiring an acid catalysis, an acidification, or the formation of an acid by-product. The six processes are: 1) decomposition of cumene hydroperoxide, 2) benzoic acid decarboxylation, 3) decomposition of sodium phenolate produced by sulfonation, 4) decomposition of sodium phenolate produced by alkaline hydrolysis of chlorobenzene, 5) catalytic hydrolysis of chlorobenzene, 6) dehydrogenation of cyclohexanol, and 7) BPA by-product cracking. These seven processes are hereinafter discussed to demonstrate the general applicability of the present invention.

Decomposition of cumene hydroperoxide

Briefly summarized the decomposition of cumene hydroperoxide comprises alkylation of benzene to cumene, oxidation to cumene to cumene hydroperoxide, followed by cleavage of cumene hydroperoxide to phenol and acetone. A typical process will involve the use of three or four cumene oxidation reactors in series. Fresh and recycled cumene is fed to a first reactor and air or oxygen is bubbled into the bottom of the reactor and exits at the top. If a reaction promoter is used there may be a layer of 2–3% aqueous sodium hydroxide in the bottom of the reactor. The reaction temperature decreases through the reactor series from about 115° C. to 90° C. in the last reactor. Generally the conversion in the first reactor is 9–12%, that in the second 15–20%, that in the in the third 24–29%, and in the last 32–39% with an overall yield through the reactor train of 90–95% by weight. The residence time in each reactor is roughly 3–6 hours. The cumene hydroperoxide is concentrated by evaporation to a solution that is 75–85 wt. % cumene hydroperoxide. Unreacted cumene hydroperoxide is recovered by distillation and recycled to the first reactor.

Cleavage of cumene hydroperoxide occurs under acidic conditions with agitation at a temperature of 60°–100° C. using various non-oxidizing inorganic acids or acid anhydrides, e.g. sulfur dioxide (hydrolyzed to sulfurous acid). Since phenols are inhibitors for free-radical oxidation processes, it is essential that no acidic materials interfere with the oxidation process. The solution in the cleavage reactor is a mixture of phenol, acetone, and various by-product compounds such as cumylphenols, acetophenone, dimethylphenylcarbinol, and α-methylstyrene. The resulting solution may be neutralized with a sodium phenoxide solution, another suitable base or passed over an ion-exchange resin. Process water may be added to assist in the removal of inorganic salts resulting from the neutralization of process acid or acid by-products. The resulting product may then be separated, washed and/or directly distilled.

Decomposition of benzoic acid

Toluene is oxidized to benzoic acid by a liquid phase free radical oxidation. After purification, the resulting benzoic acid product is decarboxylated or oxydecarboxylated to phenol either as the molten benzoic acid or in a high boiling solution, typically with a solvent boiling in the range of 220°–250° C. in the presence of steam and air and a suitable catalysts, typically a copper salt catalyst. Variations on this process exist such as a vapor-phase oxidation of benzoic acid over a copper catalyst to produce the phenol directly.

De-sulfonation of benzene sulfonic acid (decomposition of sodium phenate)

Benzene is sulfonated with sulfuric acid at a temperature of 110°–150° C. with an excess of sulfuric acid followed by neutralization of the resultant benzenesulfonic acid with alkali, usually sodium hydroxide. The benzenesulfonic acid is decomposed in molten sodium hydroxide at 320°–340° C. to form sodium phenolate. Treatment with sulfur dioxide forms sodium sulfite and releases phenol.

Hydrolysis of chlorobenzene

Benzene is chlorinated in a liquid phase catalytic chlorination employing ferric chloride as the chlorination catalyst at temperatures ranging from 25°–50° C. The resultant chlorobenzene is hydrolyzed using a caustic solution of 10–15 wt. % sodium hydroxide at temperatures ranging from 360°–390° C. under high pressure, 280–300 atm (28–30 MPa). Hydrogen chloride (hydrochloric acid) releases the phenol from the sodium phenate (phenolate).

Catalytic hydrolysis of chlorobenzene

A variation of the chlorobenzene process involves the synthesis of chlorobenzene by a catalytic oxychlorination over a cupric chloride, ferric chloride on alumina catalyst using air hydrogen chloride mixtures. The resulting chlorobenzene is catalytically hydrolyzed over a silica supported calcium phosphate catalyst under reducing conditions obtained by the presence of hydrogen at temperatures of 400°–450° C.

Cyclohexanol dehydrogenation—Cyclohexane is oxidized to cyclohexanol and cyclohexanone followed by catalytic dehydrogenation over a group VIII metal catalysts such as platinum on activated carbon or nickel cobalt on alumina. The phenol product, which forms an azeotropic mixture with cyclohexanone, is separated by an extractive process such as liquid-liquid extraction. By comparison to the previous five processes, this process has very unfavorable process economics and is no longer employed commercially to any great extent. Of the seven processes, this process is the only process where acid workup or catalysis by acidic species such as the Bronsted acids sulfuric and hydrochloric acids or the Lewis acids such as ferric chloride and the like is not employed.

Cracking of By-Products from Bisphenol Manufacture

In the process of manufacturing various bisphenol compounds by-products result therefrom. These by-products are typically recycled to a cracking reactor where they are reconverted to the phenolic precursors. Cracking of bisphenol by-products typically involves catalysis by strong acids or bases. Generally, strong acid cracking gives better yields of the phenolic compounds desired. The cracking process is generally conducted at temperatures ranging from 150° to 400 ° C. This cracking process does not synthesize phenol directly but cracks the products synthesized from phenol back to phenol.

The six commercially significant processes all employ either a Bronsted acid or a Lewis acid in the reaction scheme to produce phenol. The Bronsted acids such as sulfuric acid, arylsulfonic acids, or hydrochloric acid may leave direct contaminating trace quantities in the process stream. The Lewis acids such a ferric chloride, zinc chloride, cupric chloride, aluminum chloride, and the like suffer hydrolysis forming Bronsted acids, e.g. hydrochloric acid, that again may directly contaminate the process stream. Further when ion-exchange resins are utilized anywhere in the process, decrepitation of the resin has been observed leading to a contamination of the process stream downstream of the ion-exchange resin bed by a polymeric acidic resinous material. The presence of acids in phenol catalyze undesired decomposition and by-product reactions in further downstream processing such as distillation. The presence of trace quantifies of acids in phenol may persist beyond the use of phenol as a reagent and subsequently also catalyze undesired reactions in the product materials that are subsequently synthesized therefrom. Therefore, it is desirable to remove the various acidic components present in phenol process streams before undesired reactions are catalyzed thereby.

SUMMARY OF THE INVENTION

The present invention comprises a process for the removal of acidic impurities from phenol or phenol type compounds comprising contacting a process stream containing the phenol or phenol type compounds with an amphoteric inorganic oxide adsorbent selected from the group consisting of alumina, titania, silica, silica-alumina, magnesia, zeolites, and aluminosilicate clays. Preferably the amphoteric inorganic oxide has a BET surface area ranging from about 25 $m^2/g$ to about 700 $m^2/g$, more preferably when the amphoteric inorganic oxide is amorphous the BET surface area ranges from about 50 $m^2/g$ to about 450 $m^2/g$.

The present invention further comprises contacting a process stream containing phenol, phenol-type compounds or substituted phenols and substituted phenol-type compounds whereby trace acidic components having an acid dissociation constant greater than the component present in the process stream in the greatest quantity are reduced in concentration by being adsorbed onto the amphoteric inorganic oxide. Thus one embodiment of the present invention would be to reduce the concentration of acidic species having an acid dissociation constant greater than phenol present in a phenol containing process stream by being adsorbed onto an amphoteric inorganic oxide such as alumina.

The present invention further comprises regeneration of the amphoteric inorganic oxide by contacting an adsorbent containing adsorbed acidic components adsorbed from a particular process stream with an alkaline solution, the solution being rendered alkaline by containing alkali metal, alkaline earth, or ammonium ions.

The present invention further comprises a method of controlling the color of phenol bisphenol mixtures.

In a preferred embodiment the present invention comprises a process for the purification of phenolic compounds comprising preparing a phenolic compound by a process selected from the group consisting of decomposition of cumene hydroperoxide, the decomposition of benzoic acid, the de-sulfonation of benzene sulfonic acid, the hydrolysis of chlorobenzene, the catalytic hydrolysis of chlorobenzene, the catalytic dehydrogenation of cyclohexanol, and the cracking of by-products from the manufacture of bisphenol compounds, and purifying the phenolic compound by contacting the phenolic compound with an inorganic oxide adsorbent selected from the group consisting of alumina, titania, silica, silica-alumina, magnesia, zeolites, and aluminosilicate clays.

DETAILED DESCRIPTION OF THE INVENTION

According to the invention, a high purity phenol or substituted phenol can be produced in high yield by contacting a reaction product mixture containing a phenol with an inorganic oxide adsorbent. The reaction product mixture is the effluent of reaction zone wherein a phenol is produced from by a process selected from the group consisting of the decomposition of cumene hydroperoxide, the decomposition of benzoic acid, the de-sulfonation of benzene sulfonic acid, the hydrolysis of chlorobenzene, the catalytic hydrolysis of chlorobenzene, the catalytic dehydrogenation of cyclohexanol, and BPA by-product cracking.

The phenolic compounds which are purified by the process of the present invention are any compounds containing an hydroxy group linked to a carbon of an aromatic group. Suitable phenolic compounds, include but are not limited to phenols, substituted phenols, cresols, naphthols, phenanthrols, their homologues and analogs. Among the more industrially important of these are phenol, cresol, xylenol, chlorophenol, thymol, carvacol, cumenol, 2-methyl-6-ethylphenol, 2,4-dimethyl- 3-ethylphenol, 4-ethylphenol, 2-ethyl-4-methylphenol, 2,3,6-trimethylphenol, 2-methyl-4-tertiary-butylphenol, 2,4-ditertiarybutylphenol, 4-methyl-2-tertiarybutylphenol, 2-tertiarybutyl-4-methylphenol, 2,3,5, 6-tetramethylphenol, 2,6,-dimethylphenol, 2,6-ditertiarybutylphenol, 3,5-dimethylphenol, 3,5-diethylphenol, 2-methyl- 3,5-diethylphenol, o-phenylphenol, p-phenylphenol, and the like.

In order to obtain phenols with improved yields and higher purifies according to the process of the present invention, the effluent from the reaction zone is contacted with an inorganic oxide adsorbent under conditions wherein acidic impurities are adsorbed onto the adsorbent. The preferred inorganic oxide adsorbents are any amphoteric oxide substrates, which are oxides that have the capacity to behave either as an acid or base. The preferred amphoteric oxides will generally have an isoelectric point that is above the pH of the effluent such that the inorganic oxide will act as a weak base ion exchanger, thereby adsorbing acidic components. Examples of suitable oxides that may be employed are alumina, titania, silica, silica-alumina, magnesia, zeolites, and aluminosilicate clays. A preferred amphoteric porous inorganic oxide adsorbent is a high surface area alumina. When alumina is used as the adsorbent, the BET surface area of the alumina should be in the range from about 50 to about 450 $m^2/g$, more preferably in the range of from about 100 to about 325 $m^2/g$ and most preferably from about 125 to about 250 $m^2/g$.

The reaction mixture product effluent is preferably contacted with a fixed bed inorganic oxide adsorbent either in an upflow or downflow configuration wherein the weight hourly space velocity is within the range of from about 0.1 to about 100, preferably from about 1 to 20, and most preferably from about 1 to 10. The weight hourly space velocity may vary considerably within the scope of the invention depending to some extent upon the specific phenolic compounds being treated, the adsorbent being used, and the quantity of acidic components present with the phenolic compounds as the effluent enters the fixed bed reactor. The adsorbent may be utilized in a variety of physical forms such as pellets, extrudates, spheres, rings, cylinders, and the like.

Subsequent to being contacted by the inorganic oxide adsorbent the phenolic compound containing process stream then may be subjected to process steps that recover the phenolic compound. Suitable process include among others distillation, solvent extraction, stratification, extractive distillation, adsorption, crystallization, filtration, centrifugation, and the like.

The invention offers a number of process advantages. Phenolic compounds purified by the process of the present invention exhibit an improved thermal stability and color retention. Thus in many chemical processes employing the process of the present invention, the phenolic compounds may be used directly after recovery without the need for a purifying step involving a thermal treatment such as a distillation.

When a fixed bed adsorption process is utilized to purify phenolic compound containing process streams, the inorganic oxide adsorbent utilized for the adsorption of the acidic contaminants may be regenerated by washing the bed with a basic solution containing ammonium or alkali metal salts that render the wash solution basic, that is having a pH above 7.

The following examples illustrate the acid removal step in a process comprising the production of a phenolic compound and the removal of acidic impurities by contacting the reaction mixture product effluent with an inorganic oxide adsorbent. The examples are not intended to limit the scope of the claims appended hereto.

EXPERIMENTAL

A 1 liter sample of pure phenol was stirred for about 30 minutes with 300 grams of a commercial sulfonated polystyrene ion exchange resin that had been previously dried under vacuum. After removing the ion exchange resin by filtration, the resulting treated phenol was diluted with 1.5 liters of fresh phenol to an acidic polystyrene oligomer concentration of approximately 66 ppm, based on titration results. This solution was prepared as a standard stock solution to test the concept of the invention and reduce the invention to practice. 170 gram portions of the phenol mixture were separately treated by stirring for a period of ten minutes with the following amphoteric porous inorganic oxide materials: 1) 15 grams silica gel obtained from Davison Chemicals, 2) 5 grams of neutral alumina obtained from Fisher Scientific, 3) 15 grams of basic alumina obtained from Fisher Scientific, and 4) 15 grams of titanium oxide obtained from American Cyanamid. The oxides were filtered from the solution and subsequently discarded. The phenol mixture was then analyzed for acidic oligomer content. A 150 gram portion from each test was then mixed with 150 grams of bisphenol-A and heated to 210° C. for a period of four hours followed by a high pressure liquid chromotography analysis. After heating for 4 hours and analyzing by high pressure liquid chromatography, the phenol bisphenol-A mixture was also analyzed for color. The color value was determined by reporting 10 times the absorbance of a 1% solution of the material through a 10 cm path length spectrometer cell. Samples having a color value greater than 20 were diluted with methanol before analyzing and the result obtained was multiplied by the dilution factor. On this scale, pure colorless phenol has a color value of 0.5. The results of the experiments are summarized in Table 1:

TABLE 1

| | Adsorption of Acidic Contaminants from Phenol | | | | |
|---|---|---|---|---|---|
| | Acid Conc. (Final) | | Amount of | % of BPA | |
| Inorganic Oxide | ppm | % of Fresh | BPA Remaining | Lost by Degradation | Resulting Color |
| None (Control) | 66 | 100 | 40–48 g | 68–73 | 28–54 |
| Silica Gel | 16 | 24 | 146.6g | 2 | 18 |
| Titanium Oxide | 5 | 7 | 128.5 | 13.8 | 30 |
| Alumina (neutral) | 0 | 0 | 150.0 | 0 | 0.9 |
| Alumina (basic) | 14.5 | 22 | 116.9 | 21 | 18 |

While the experiment reducing the invention to practice most closely simulates a stirred tank reactor configuration, commercial applications would most likely utilize a fixed bed reactor process configuration either in an upflow or downflow process configuration. Engineering considerations and process economics as understood by a practitioner having ordinary skills in the art will dictate the precise configuration appropriate for a given industrial installation.

Having described the invention, that which is claimed is:

1. A process for the purification of a phenolic compound comprising:
    a) preparing a phenolic compound by a process selected from the group consisting of decomposition of cumene hydroperoxide, the decomposition of benzoic acid, the de-sulfonation of benzene sulfonic acid, the hydrolysis of chlorobenzene, the catalytic hydrolysis of chlorobenzene, the catalytic dehydrogenation of cyclohexanol, and the cracking of by-products from the manufacture of bisphenol compounds, and
    b) purifying the phenolic compound by contacting the phenolic compound with an inorganic oxide adsorbent selected from the group consisting of alumina, titania, and magnesia.

2. A process for the removal of acidic contaminants from a process stream comprising a phenolic compound comprising:
    a) preparing a phenolic compound by a process selected from the group consisting of decomposition of cumene hydroperoxide, the decomposition of benzoic acid, the de-sulfonation of benzene sulfonic acid, the hydrolysis of chlorobenzene, the catalytic hydrolysis of chlorobenzene, the catalytic dehydrogenation of cyclohexanol, and the cracking of by-products from the manufacture of bisphenol compounds, and
    b) purifying the phenolic compound by contacting the phenolic compound with an inorganic oxide adsorbent selected from the group consisting of alumina, titania, and magnesia whereby the concentration of said acidic contaminants in said process streams containing said phenolic compounds is reduced.

3. A process for the removal of acidic contaminants from a process stream comprising a phenolic compound consisting essentially of:

a) preparing a phenolic compound by a process selected from the group consisting of decomposition of cumene hydroperoxide, the decomposition of benzoic acid, the de-sulfonation of benzene sulfonic acid, the hydrolysis of chlorobenzene, the catalytic hydrolysis of chlorobenzene, the catalytic dehydrogenation of cyclohexanol, and the cracking of by-products from the manufacture of bisphenol compounds, and b) purifying the phenolic compound by contacting the phenolic compound with an inorganic oxide adsorbent selected from the group consisting of alumina, titania, and magnesia whereby the concentration of said acidic contaminants in said process streams containing said phenolic compounds is reduced.

4. The process of claim 1 wherein the phenolic compound being purified comprises phenol.

5. The process of claim 1 wherein the phenolic compound being purified consists essentially of phenol.

6. The process of claim 1 wherein the inorganic oxide adsorbent is alumina.

7. The process of claim 1 wherein the phenolic compound is selected from the group consisting of phenol, cresol, xylenol, chlorophenol, thymol, carvacol, cumenol, 2-methyl-6-ethylphenol, 2,4-dimethyl-3-ethylphenol, 4-ethylphenol, 2-ethyl-4-methylphenol, 2,3,6-trimethylphenol, 2-methyl-4-tertiary-butylphenol, 2,4-ditertiarybutylphenol, 4-methyl-2-tertiarybutylphenol, 2-tertiarybutyl-4-methylphenol, 2,3,5,6-tetramethylphenol, 2,6,-dimethylphenol, 2,6-ditertiarybutylphenol, 3,5-dimethylphenol, 3,5-diethylphenol, 2-methyl- 3,5-diethylphenol, o-phenylphenol, and p-phenylphenol.

8. The process of claim 4 wherein the inorganic oxide adsorbent is alumina.

9. The process of claim 7 wherein the inorganic oxide adsorbent is alumina.

10. The process of claim 2 wherein the phenolic compound is selected from the group consisting of phenol, cresol, xylenol, chlorophenol thymol, carvacol, cumenol, 2-methyl-6-ethylphenol, 2,4-dimethyl-3-ethylphenol, 4-ethylphenol, 2-ethyl-4-methylphenol, 2,3,6-trimethylphenol, 2-methyl-4-tertiary-butylphenol, 2,4-ditertiarybutylphenol, 4-methyl-2-tertiarybutylphenol, 2-tertiarybutyl-4-methylphenol, 2,3,5,6-tetramethylphenol, 2,6,-dimethylphenol, 2,6-ditertiarybutylphenol, 3,5-dimethylphenol, 3,5-diethylphenol, 2-methyl- 3,5-diethylphenol, o-phenylphenol, and p-phenylphenol.

11. The process of claim 10 wherein the inorganic oxide adsorbent is alumina.

12. The process of claim 3 wherein the phenolic compound is selected from the group consisting of phenol, cresol, xylenol, chlorophenol, thymol, carvacol, cumenol, 2-methyl-6-ethylphenol, 2,4-dimethyl-3-ethylphenol, 4-ethylphenol, 2-ethyl-4-methylphenol, 2,3,6-trimethylphenol, 2-methyl-4-tertiary-butylphenol, 2,4-ditertiarybutylphenol, 4-methyl-2-tertiarybutylphenol, 2-tertiarybutyl-4-methylphenol, 2,3,5,6-tetramethylphenol, 2,6,-dimethylphenol, 2,6-ditertiarybutylphenol, 3,5-dimethylphenol, 3,5-diethylphenol, 2-methyl- 3,5-diethylphenol, o-phenylphenol, and p-phenylphenol.

13. The process of claim 12 wherein the inorganic oxide adsorbent is alumina.

14. The process of claim 1 wherein the inorganic oxide adsorbent is regenerated by washing said adsorbent with a solution having a pH greater than 7, said solution comprising ammonium or alkali metal salts.

15. The process of claim 2 wherein the inorganic oxide adsorbent is regenerated by washing said adsorbent with a solution having a pH greater than 7, said solution comprising ammonium or alkali metal salts.

16. The process of claim 3 wherein the inorganic oxide adsorbent is regenerated by washing said adsorbent with a solution having a pH greater than 7, said solution comprising ammonium or alkali metal salts.

* * * * *